(12) United States Patent
Papirov et al.

(10) Patent No.: US 11,213,453 B2
(45) Date of Patent: Jan. 4, 2022

(54) TREATMENT FOR LARGE VOLUME BIOLOGICAL TARGETS WITH A HIGH PRESSURE SHOCKWAVE INSTRUMENT

(71) Applicant: HI IMPACTS LTD, Petach Tikva (IL)

(72) Inventors: Eduard Papirov, Hod Hasharon (IL); Itzhak Friedman, Kiryat Ono (IL); Yehoshua Dolberg, Raanana (IL)

(73) Assignee: HI IMPACTS LTD, Petach Tikva (IL)

( * ) Notice: Subject to any disclaimer, the term of this patent is extended or adjusted under 35 U.S.C. 154(b) by 890 days.

(21) Appl. No.: 15/538,254

(22) PCT Filed: Dec. 21, 2015

(86) PCT No.: PCT/IL2015/051238
§ 371 (c)(1),
(2) Date: Jun. 21, 2017

(87) PCT Pub. No.: WO2016/103257
PCT Pub. Date: Jun. 30, 2016

(65) Prior Publication Data
US 2017/0360654 A1     Dec. 21, 2017

Related U.S. Application Data

(60) Provisional application No. 62/095,015, filed on Dec. 21, 2014.

(51) Int. Cl.
*A61H 23/00*     (2006.01)
*A61B 17/22*     (2006.01)
*A61N 7/00*      (2006.01)
*A61D 1/00*      (2006.01)
*A61B 17/225*    (2006.01)

(52) U.S. Cl.
CPC ..... *A61H 23/008* (2013.01); *A61B 17/22004* (2013.01); *A61B 17/225* (2013.01); *A61D 1/00* (2013.01); *A61N 7/00* (2013.01); *A61H 2201/5058* (2013.01);
(Continued)

(58) Field of Classification Search
None
See application file for complete search history.

(56) References Cited

U.S. PATENT DOCUMENTS 2,931,947 A * 4/1960 Fruengel ............... A01J 7/02
                                                         315/111.01
5,285,772 A * 2/1994 Rattner ............. A61B 17/2255
                                                           378/205
(Continued)

FOREIGN PATENT DOCUMENTS

CN          200991282      * 12/2007   .......... A61B 17/225
WO    WO-2013114366 A1 *  8/2013   ....... A61B 17/22004

OTHER PUBLICATIONS

English translation for CN200991282, translated on espacenet.com, translated on Nov. 19, 2020.*

*Primary Examiner* — Tu A Vo
(74) *Attorney, Agent, or Firm* — The Law Office of Joseph L. Felber

(57) ABSTRACT

The present invention relates to a device, system and a method for high pressure shockwave treatment of biological tissue having a large treatment zone and in particular to such a device, system and method in which a large biological treatment area in treated in a non-drug, non-surgical treatment protocol utilizing ballistic shockwave generating device.

32 Claims, 10 Drawing Sheets

(52) U.S. Cl.
CPC .................. *A61N 2007/006* (2013.01); *A61N 2007/0013* (2013.01); *A61N 2007/0034* (2013.01)

(56) References Cited

U.S. PATENT DOCUMENTS

| | | | |
|---|---|---|---|
| 7,485,101 B1* | 2/2009 | Faragalla | A61B 17/22 600/437 |
| 2006/0100550 A1* | 5/2006 | Schultheiss | A61H 23/0245 601/2 |
| 2008/0000426 A1* | 1/2008 | Grabek | A01J 5/0135 119/14.14 |
| 2010/0094134 A1* | 4/2010 | Zhu | A61B 5/0073 600/473 |
| 2016/0310766 A1* | 10/2016 | Cioanta | A61N 7/00 |

\* cited by examiner

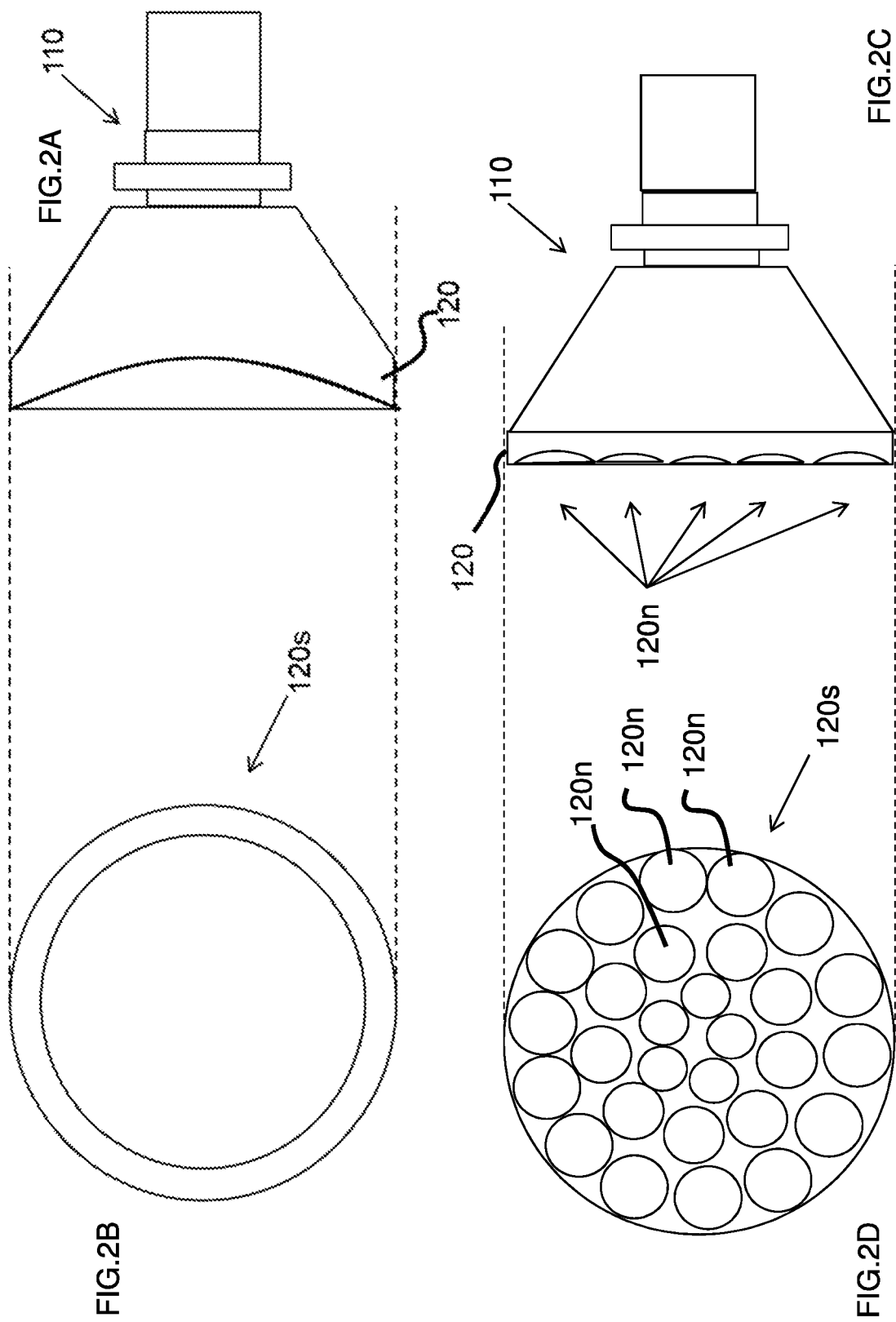

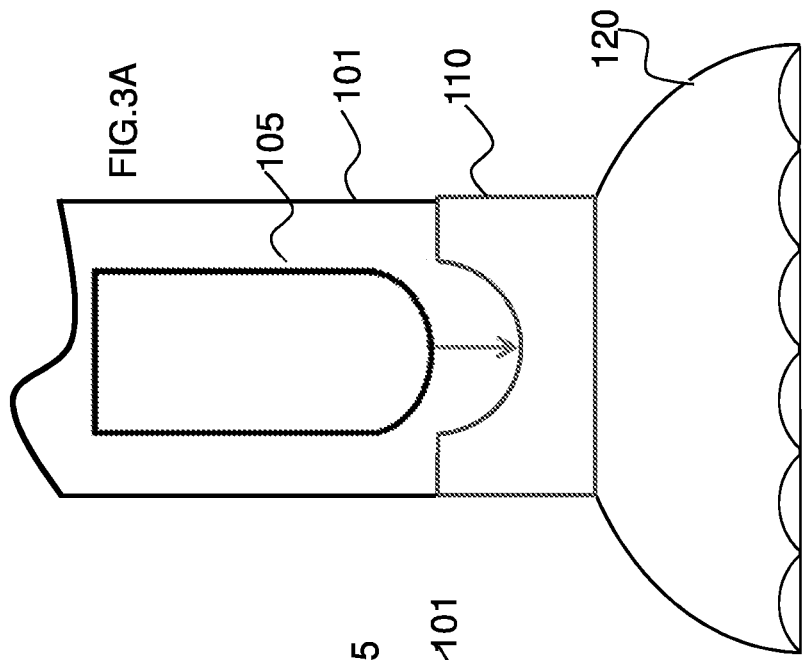
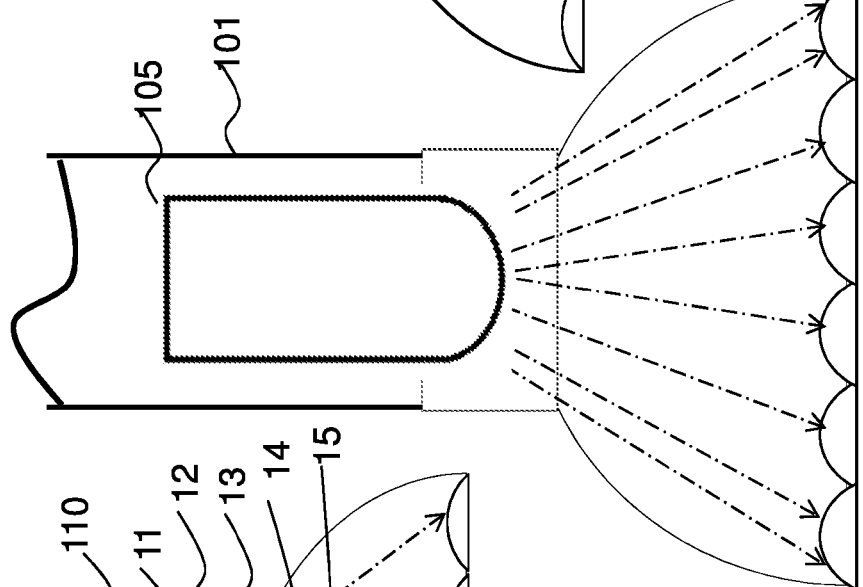
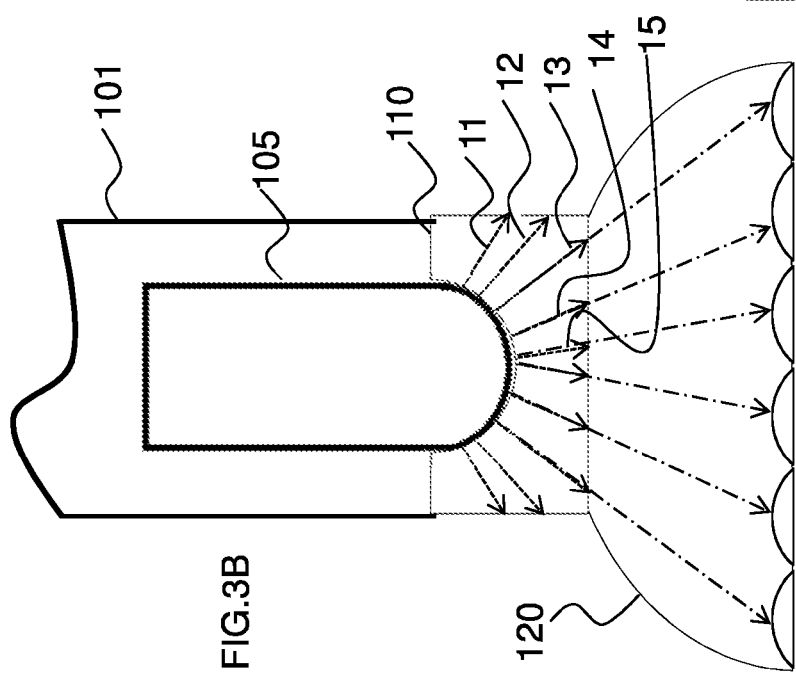

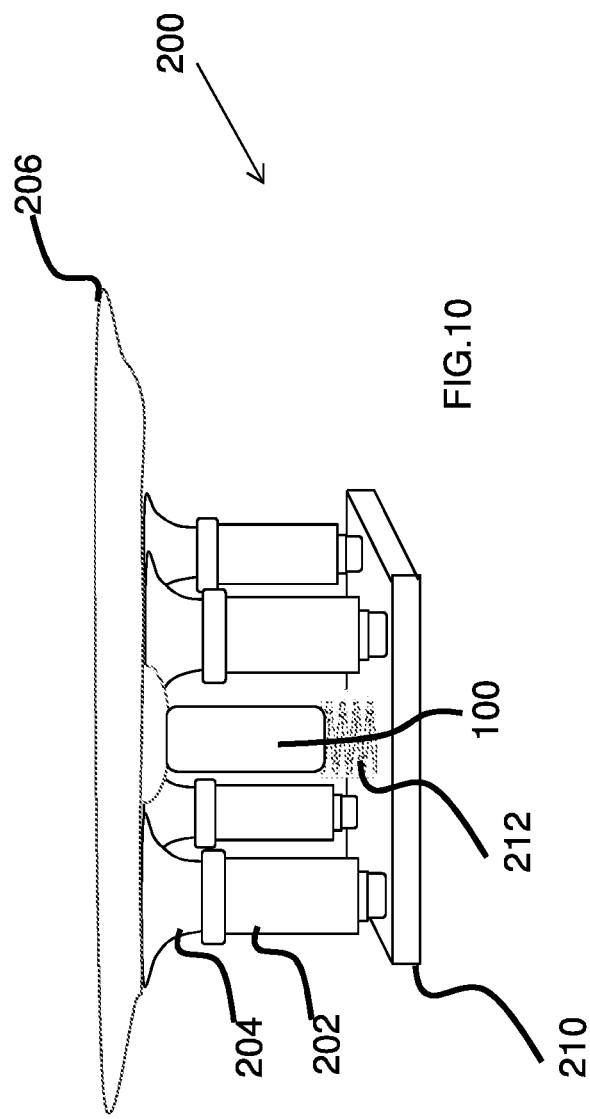

TREATMENT FOR LARGE VOLUME BIOLOGICAL TARGETS WITH A HIGH PRESSURE SHOCKWAVE INSTRUMENT

CROSS REFERENCE TO RELATED APPLICATION

This application claims priority to U.S. Provisional Patent Application No. 62/095,015, filed Dec. 21, 2014, entitled "Treatment for Large Volume Biological Targets with a High Pressure Ballistic Shockwave Instrument," the disclosure of which is incorporated herein by reference in its entirety.

FIELD OF THE INVENTION

The present invention relates to a device, system and a method for high pressure shockwave treatment of biological tissue having a large treatment zone and in particular to such a device, system and method in which a large biological treatment area in treated in a non-drug, non-surgical treatment protocol utilizing ballistic shockwave generating device.

BACKGROUND OF THE INVENTION

Shockwave therapy (SWT) is a non-invasive form of treatment for various medical conditions using acoustic Shockwaves. The use of shockwaves is perhaps best known for its use in fragmentation of kidney stones in a process called lithotripsy. However shockwaves have also been used for other indications such as healing bone fractures, chronic orthopedic inflammation, wound healing of chronic wounds, treatment of heart muscle ischemia as well as other medical condition as is known in the art.

Acoustic Shockwaves may be generated by a variety of force generators, including electrohydraulic electromagnetic, piezoelectric and ballistic force generators.

In ballistic shockwave generators, shockwaves are generated by high-energy collisions between two masses, with the energy propagating through a metallic media and shaped as a focused of diffused wave front starting from the geometric edge and propagating toward the treated biological tissue.

Shockwaves generating devices and system are generally coupled with the tissue being treated with fluid coupling such as gel or a balloon so as to allow for the generated shockwaves to enter the target tissue.

Shockwaves are distinct from mechanical pressure waves having specific characteristics. A pressure wave is a general term for a pressure disturbance moving through a medium. This happens to be exactly what a sound wave is. These disturbances move at the speed of sound in the medium in which they are traveling. There is no formal distinction between the two, as any amplitude of pressure wave could be heard as sound provided the listening device is sensitive enough.

A shockwave however has a specific type of pressure disturbance moving through a fluid medium. For small amplitudes, sound pressure waves pass through the medium, which then more or less returns to its initial state. However, a wave with large enough amplitude will drag a little bit of the medium along with it. That means that sound waves propagating behind it will tend to catch up with the original wave and drag the fluid behind them still faster. That process stacks up and eventually you can have a number of pressure waves that coalesce into a shockwave.

Although sharing several common properties, shockwaves differ from mechanical pressure waves in the important feature of pulse duration. The energy wavefront of true shockwaves is concentrated within several microseconds (0.25 to 4 microseconds, when measured according to IEC61846 and commonly between 0.5-1 microsecond), while the energy of a pressure wave is dispersed over several milliseconds (1 to 7 milliseconds, regularly). A shockwave pulse has a rise-time of 300 nanoseconds occurs within 1 microsecond from pulse start and a mechanical pressure pulse starts approximately 1 millisecond later.

This distinction between mechanical pressure waves and shockwaves determines the penetration of the wave energy; while mechanical pressure waves mainly affect the surface tissue, the short duration of the pressure pulse of shockwaves has limited interaction with surface tissue and the shockwaves energy propagates into the tissue and has more effect on inner body structures.

SUMMARY OF THE INVENTION

There is an unmet need for, and it would be highly useful to have, a system and a method providing a shockwave treatment of a large tissue volume, wherein the shockwave system provides for deep penetration of shockwaves to treat a human or animal body.

The present invention generally relates to medical systems that produce ballistic shockwaves for extracorporeal treatment of large treatment zones of biological tissues of the human or animal body.

More specifically, the invention relates to medical systems that produce high-pressure ballistic shockwaves that enable the targeting of large volume for treatment tissue. As a non-limiting embodiment of the present invention provides a shockwave generating device, in the form of a ballistic shockwave device with an operational pressure of higher than 50 bar and up to about 200 bar that in enables treatment of a large target area that are typically characterized by diameters between 30 mm and 300 mm, for example as described in co-owned PCT Patent Publication No. WO/2013/114366, detailing a high pressure ballistic shockwave the disclosure of which is incorporated herein by reference in its entirety.

Optionally with such shockwave generating device the treatment target area may be characterized by dimensions larger than 80 mm and lower than 200 mm.

The present invention provides a high-pressure ballistic shockwaves system, comprising: a shockwaves applicator for high-pressure shockwaves that comprises a projectile, a projectile accelerator and a shockwave generating surface that are configured to repeatedly propel a projectile to collide with the shockwave generating surface, so that the collision generates a high-pressure shockwave; a shockwave shaping portion that is configured to be mechanically coupled to the shockwave generating surface for most efficient propagation of shockwaves and utilizes at least one shockwave focal surface for converting the generated shockwaves to a shape that is required for essentially preferred treatment of the target tissue.

The shockwave shaping portion may be provided in any geometric shape. Most preferably shockwave shaping portion is provided in a spherical, circular and/or ovoid configuration having a diameter of up to about 100 mm. Optionally shaping portion may be provided with a diameter of about 50 mm. Optionally shaping portion may be provided with a diameter of up to about 150 mm. Optionally shaping portion may be provided with a diameter from about 10 mm and up to about 100 mm.

In embodiment the shock-wave shaping portion comprises several shockwave focal surfaces that together shape the shockwaves for treatment of a large target volume, for example a quarter of a bovine udder.

Optionally the shockwave applicator comprises a gaseous high pressure source and a high pressure flow controller to energize and propel the projectile in a fast and controllable manner.

In embodiments the system includes also an essentially liquid shockwaves propagation medium that enables the propagation of the shockwaves from the shockwaves shaping portion to the target treatment volume and essentially filters out the mechanical pressure waves that mainly affect the treatment target surface, with just minimal penetration into the volume.

Optionally the system may include a locating sensor for positioning the shockwave generating surface essentially onto a treatment area.

Optionally the system may include a feedback device that provides a signal that indicates treatment parameters.

Optionally the high-pressure ballistic shockwaves system may be configured to enable easy mounting and switching between different shockwaves shaping portions according to parameters relating to the specific treatment target site.

Optionally the high-pressure ballistic shockwaves system is configured for the treatment of large treatment targets, such as essentially the full volume of a quarter of bovine udder, the human trochanter fascia covering the piriformis muscle or human groin. In a preferred embodiment, the shockwaves system can be fit with shockwaves shaping portions that affect treatment targets that have typical dimensions of 50 to 300 mm in diameter and width and 50 mm to 200 mm in depth. More specifically: between 120 mm to 250 mm in diameter and 50 to 150 mm in depth.

In specific cases, such as the piriformis muscle syndrome and other human fascia-related disorders, there are significant benefits to concurrently treating an entire target area instead of scanning that same area and treating a point at a time. Point scans take longer, cause topical pain at the skin contact area and introduce stress between treatment points—where each of these phenomena may render the treatment impractical, while concurrent treatment of an entire lesion is faster, may need smaller number of shockwaves, reduce pain and result in an equivocal treatment of the full target area.

The ability to generate high-pressure shockwaves and shape the generated shockwaves to a specific array of focal areas at specific target depths enables the treatment of several clinical targets for example including but not limited to: treatment of bovine udder quarter that is infected with chronic mastitis, treatment of bovine udder quarter that is infected with sub-clinical mastitis, treatment of bovine udder quarter that yields a significantly reduced quantity of milk and/or protein and/or sugar, treatment of all quarters of bovine udder during the lactation cycle dry period, treatment of bovine tendons and ligands to reduce stress and limping, or the like.

In embodiments, the high-pressure ballistic shockwaves system may be configured for the treatment of other large mammal treatment targets, for example including but not limited to: treatment of buffalo udder quarters, treatment of goat udder halves, treatment of sheep udder halves, treatment of tendons and ligands to reduce stress and limping, or the like.

In embodiments, the high-pressure ballistic shockwaves system may be configured for the treatment of other large human musculoskeletal treatment targets, for example including but not limited to: treatment of trochanter fascia to address piriformis syndrome, treatment of groin pain, including such caused by enthesopathy, treatment of the hip osteoarthritis, including such that is caused by femoroacetabular impingement, treatment of thoracolumbar fascia to address shear strain in low back pain, or the like.

In embodiments the high-pressure ballistic shockwaves system may be configured to be located against the bovine udder in attachment to milking equipment such as a milking robot, where the small size and light weight enable the mounting of the shockwave system on the teats suction cups. The four teats suction cups are used as means to provide a mechanical mounting support and an essentially exact location that relates to the connection tissue between the udder quarters.

Optionally a spring may be provided between the suction cups and the shockwaves system to ensure that the shockwave generating system is pressed against the bovine udder.

Optionally a locating sensor disposed on the shockwave generating system may comprise a laser pointer that provides visual indication of the center of the treatment target to facilitate placement of the shockwave system. Optionally the exact position and orientation of the shockwaves system may be mechanically adjusted relative to the suction cups.

Optionally the effect of pressing the shockwave generating portion against the bovine udder may be achieved by an air piston that is activated after the attachment of the suction cups to the bovine teats and after the adjustment of position and inclination of the shockwave system. The air piston provides controlled and constant pressure for optimal propagation of shockwaves onto the target udder.

In a non-limiting example, this shockwaves treatment can be integrated into a regular milking process, with or without a modified automated milking system. Such milking processes often include cow identification and personalized stage processes that may include, besides milking, administering vaccinating or therapeutic materials. The shockwaves treatment can be included as one of these specific personalized stages. Positioning and orientating the shockwaves instrument can be done in reference to the cow known dimensions and position of milking suction cups.

In embodiment, the shockwaves system can be fitted with shockwaves shaping portions that propagate directional shockwaves at an angle to the shockwaves system symmetry axis, such that the acoustic wavefront will be directed toward a slanted target volumes to enable the treatment of, for example, the milk ducts in the teat cistern).

In embodiments the mechanical coupling between the shockwave generating surface and the shockwave shaping portion for efficient shockwaves propagation is implemented by machining both touching surfaces for best fit. The level of coupling strongly depends on the level of contact between the surfaces. In one preferred embodiment the surfaces are polished to a submicron level.

Optionally, the surfaces are machined to a fine level and a nano-powder of hard material is placed between the surfaces to ensure solid contact between them. Optionally this nano powder may consist of 50 nm Zirconia particles. Optionally the surfaces may be connected by brazing with thin silver compound.

For best shockwaves propagation, an essentially continuous, acoustically transmissive, liquid propagation medium is required to fill the gap between the shockwaves shaping portion and the targeted tissue site, such as the bovine udder.

Optionally the liquid propagation medium may be a gel that is enclosed in a special, thin membrane that is attached to the shockwave shaping portion. Optionally membrane is a one way leaky membrane that allows for migration of small amounts of gel when it is pressed against the treatment target surface to create an essentially continuous liquid medium that provides acoustic coupling between the shockwave shaping portion and the treatment target surface. Optionally a gel reservoir may be connected into the membrane and a pump enables replenishing of the gel medium when it is depleted.

Optionally thickness of the membrane should be minimized for optimal shockwave effect and care must be taken that the mediating volume between the shockwaves shaper and the target treated tissue is completely filled with liquid in the balloon and gel between balloon shell and the treated tissue.

In embodiments the high-pressure ballistic shockwaves system may include a feedback sensor that enables an automated feedback from propagated shockwaves. That feedback sensor is a fast pressure sensor that measures time-calibrated signal on the surface of the shockwaves shaping portion that indicates shockwaves reflection from the target surface. The pressure sensor signal is read during a predetermined window in time that is centered on the expected duration between the forward-going shockwave signal and the backward reflection from a different tissue— e.g., a bone under a fascia layer.

The forward-going pressure signal levels provide indication for the strength of the propagated shockwaves. An increase during treatment indicates deterioration in acoustic coupling that may indicate, in a non-limiting example, depletion of propagation medium.

Variance in the ratio between the forward-going signal and the reflection signal indicates changes in the intermediary fascia that are caused by the SWT. This variance is a feedback that signals the effect of SWT and can serve as an efficacy indicator for decision to stop the treatment session or the treatment completely.

To achieve a certain therapeutic effect by applying shockwaves to a treatment target, the shockwaves dose must be controlled by controlling the position, direction, the pulse energy and the number of pulses applied.

Traditionally, shockwaves instruments produce either focused shockwaves to attain high-pressure impact on a small area, or non-focused (often radial) shockwaves that attain low-pressure impact on a larger area. Focusing of shockwaves enables the concentration of energy at a specific area at a specific depth—according to the geometry of the shockwaves shaping portion of the present invention.

The invented instrument provides very high-pressure shockwaves that can be shaped by a given shockwaves shaping portion as either focused or dispersed, or a mixture of focused and dispersed for a variety of curative effects.

Embodiment of the present invention provide a shockwave shaping portion to control the depth and treatment provided to the tissue treatment site. The shockwave shaping portion provided in the form of a round surface including a plurality of depressions that are created as a spherical section. The spherical depressions provide for focusing the shockwaves to a point in general vicinity of the sphere center. Preferably the diameter of the round depression determines the area of the shockwave shaping portion from which shockwaves are accumulated to be focused, while the sphere radius determines the distance of the shockwaves focal point from the face of the shockwave shaping portion.

Embodiments of the present invention provide a ballistic shockwaves instrument creates high-pressure shockwaves that can be dispersed over a large diameter shockwave shaping portion utilizing a plurality of round surface depressions that are created as spherical sections. Most preferably the depressions create a corresponding number of shockwaves focal points.

Optionally the shockwave shaping portion may combine several surface depressions with more than one diameter wherein each accumulating a corresponding portion of shockwaves that are directed to a predesigned focal point, with a depth determined by the radius of the corresponding sphere section.

Optionally the sphere radii may differ within a single shaping portion determined according to the different depths of depressions in the shockwaves shaping portion surface, where all of them are sections of identical spheres—thus yielding focal points at the same depth.

Due to the characteristics of the medium, the shockwaves focal points are volumetric in shape and dependent on the designed distance between the focal points, they can be tangential to each other. Surface depressions can be arranged in a shockwaves shaping portion so that the resultant shockwaves focal points reside on a three dimensional focal treatment surface.

In embodiments both the projectile and shockwaves generating surface are rounded to spherical sections that fit one another. In such a design, a larger projectile area hits a larger shockwaves generating surface area at the same time and the resultant shockwaves are distributed perpendicular to each point of the spherical section.

The simplified behavior of shockwaves propagation that was described above ignored the interference between shockwaves that propagate at very close durations throughout the shockwaves shaping portion. Typically, shockwave wavefront duration is measured in fractions of microseconds so that even small differences in propagation path can have an effect on the wavefront. This interference effect is manifested more in shockwaves shaping portions of larger size. The interfering shockwaves may reach the surface depressions, but will reduce the total energy of the shockwave wavefront that will reach the treatment zone and affect the treatment. This interference effect is smaller and almost negligible when the spherical depression.

In a preferred embodiment of the present invention, each surface depression is connected to the shockwaves generating surface by a conical section that is essentially perpendicular to it. In this way only the portion of the generated shockwaves that is most effective in generating a sharp wavefront is directed toward the corresponding surface depression. By arranging the entire volume of the shockwave shaping surface in this way, the interference is reduced to minimum. While the total energy that reaches the external surface of the shockwaves shaper is lower than when the full volume is solid, the wavefronts generated by directional solid connections are more accurate and enable a more efficient treatment.

Herein, the term of dose is used for the shockwave power or energy, depending on the specific kind of treatment. It may be specified in J/cm2 (joules per centimeter squared) when referring to energy delivered into a specific volume or in J/mm2 (joules per millimeter squared) when referring to energy delivered to a specific surface area.

The dose may vary by using different pulse durations, pulse energies, pulse repetition rates, pulse counts and treatment times. Preferably, energy of 0.1 to 10 mJ/mm2, most preferably 1 to 3 mJ/mm2 is applied after correction for absorption. The preferred pulse rate is between 1 and 20, most preferably 5-10 pulses per second.

It is important to keep the dose in a certain range. There must be a minimum dose to obtain a therapeutic effect, e.g. for [thrombolysis, increased circulation, metabolism or stimulation of nerves. Exceeding a maximum dose must be prevented as this may lead to side effects like hemorrhage The efficacy of shockwave treatment ('SWT') for the treatment of inflammatory disorders was observed experimentally at first and the various effects of shockwaves on a variety of soft tissue surrounding bones of interest was researched extensively for many clinical indications. The list of indications for which experimental data on the healing effect of SWT was published in peer reviewed literature includes tendinopathies, difficult to heal and non-healing wounds, bone regeneration, ischemic muscles, burn injuries, tissue allotransplantation, murine skin isografts as well as common orthopedic disorders such as plantar fasciitis, piriformis syndrome, groin pain, hip osteoarthritis, shear strain in low back pain—and many others Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 2A-D are schematic illustrative diagrams of an exemplary shockwave shaping device according to optional embodiments of the present invention;

FIG. 3A-C are schematic illustrative diagrams of an exemplary shockwave shaping device according to embodiments of the present invention;

FIG. 10 is a schematic illustrative diagram of an exemplary shockwave system coupled to a milking machine0 according to an optional embodiment of the present invention.

DESCRIPTION OF THE PREFERRED EMBODIMENTS

The principles and operation of the present invention may be better understood with reference to the drawings and the accompanying description. The following figure reference labels are used throughout the description to refer to similarly functioning components are used throughout the specification hereinbelow.

Figure 1A:
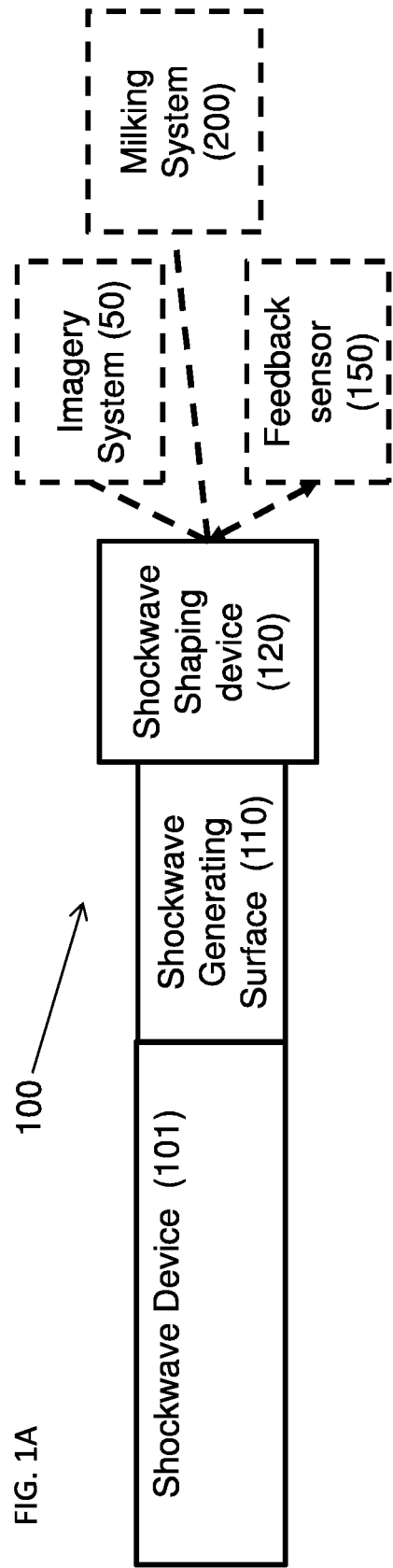
FIG. 1A-B are schematic block diagrams of an exemplary system according to embodiments the present invention.

10-18 shockwave wave front;
20 shockwave focal zone;
50 imagery system;
100 shockwave system;
101 shockwave device;
105 projectile;
110 shockwave generating surface;
120 shockwave shaping portion/adaptor/device/apparatus;
120n concave recess/depressions;
120h height;
120r radius
120s external surface;
121-128 individual concave segments;
130 rotating stage;
150 feedback sensor;
200 milking system;
202 teat suction cups;
204 teat;
206 udder;
210 milking system base/stage;
212 mounting member/support member;

FIG. 1A shows a schematic block diagram of a system 100 for providing shockwave treatment to the human or animal body. System 100 is characterized in that it is configured to provide shockwave treatment, preferably in a non-invasive manner, to a large tissue volume.

Shockwave treatment system 100 comprises a shockwave generating device 101, a shockwave generating surface 110 and a shockwave shaping portion 120, preferably in the form of a treatment applicator (treatment head).

Most preferably shockwave generating device 101 is provided in the form of a ballistic shockwave generating device utilized to propel a projectile 105 (FIG. 3A) by utilizing high pressure gaseous source to accelerate the projectile. Optionally shockwave generating device 101 may be realized in any form of shockwave device for example including but not limited to electrohydraulic, electromagnetic, piezoelectric and ballistic force generators, any combination thereof or the like shockwave generating device.

System 101 may optionally be utilized with an imagery system 50, for example medical imagery in the form of an ultrasound system, to facilitate locating and identifying an targeted treatment area. Optionally imagery system may be provided in any form as is known in the art for example including but not limited to ultrasound, CT, MRI, Doppler Ultrasound, or the like.

System 100 may be further associated with and/or functionally coupled to a milking system 200, as will be described in greater details in FIG. 10, to facilitate treatment of a cow's udder or the like animals that may be milked for example including but not limited to goats, sheep, buffalo, camel, horse or the like. Preferably system 100 may be utilizing within a milking system 200 to facilitate treating the animal population in a systemic manner to ensure the health of the animal population. In particular system 100 may be utilized to treat mastitis in cows and/or to optimize and/or improve overall milk production and health of a cow herd population.

Preferably shockwave generating device 101 is fit with appropriate mechanical components, sensors, electronics, controls and processing capabilities as is known in the art for shockwave generating devices, and in particular ballistic shockwave generating devices.

Ballistic shockwave device 101 provides for producing high pressure extracorporeal ballistic shockwaves the system comprising: a projectile accelerating portion (not shown) and at least one shockwave generating portion (110); wherein the ballistic shockwave is generated by a collision between an accelerated projectile (105) disposed within the projectile accelerating portion against a shockwave generating surface (110), the shockwave generating surface (110) is configured to withstand high pressure ballistic impact with projectile (105), wherein the generating surface (110) is coupled to shockwave shaping portion (120) providing a focal surface (120s) configured for shaping the generated shockwaves according to required treatment parameters; the projectile (105) is propelled with a gaseous high pressure source providing an operational pressure of up to about 100 bar, and a high pressure flow controller (120) to controllably energize and accelerate and reload the projectile (105) in a controllable and directed manner; the system is characterized in that it utilizes a shockwave shaping portion (120) that is adept at producing shockwave front sufficient to treat a large tissue volume and controllable depths as will be descried in greater detail.

Shockwave generating device 101 may optionally be associated with a feedback sensor 150, that is provided to ensure that system 100 and in particular device 101 is producing the correct shockwaves signals 10 as planned.

Shockwave generating device 101 is preferably provided in the form of a ballistic shockwaves generating device that is adept at producing high-pressure shockwaves by accelerating a projectile (105) under high pressure through a projectile accelerator (not shown) toward shockwave generating surface 110 to produce high-pressure shockwaves. Device 101, projectile 105 and generating surface 110 are provided from materials configured to allow for repeated collision to generate the high-pressure shockwaves.

Most preferably generating surface 110 is provided from metals and/or metallic alloys, that are configured to endure and withstand repeated collision with projectiles under high pressure, and sufficient to produce high pressure shockwaves.

Most preferably generating surface 110 is shaped and sized so as to allow it to endure and withstand repeated collision with projectiles under high pressure, while allowing for producing high pressure shockwaves. Optionally and preferably generating surface 110 may be configured according to the shape and size of projectile 105 used with device 101. Preferably generating surface 110 is provided in a concave configuration, for example as shown in FIG. 3A-C. The concave configuration of surface 110 provides for optimizing shockwave production.

Preferably shockwave generating surface 110 is functionally associated with shockwave shaping portion 120, so as to allow for the optimal transfer of shockwaves generated by surface 110 to propagate through shaping portion 120 and therefrom onto the treatment tissue.

Optionally and preferably surface 110 is functionally associated and/or coupled with shaping portion 120 such that they are fluid and/or seamless with one another. Preferably shaping portion 120 is mechanically coupled with shockwave generating surface 110 to provide for efficient shockwave propagation. Optionally and preferably coupling may be implemented by machining both corresponding surfaces so as to best fit with one another. Optionally, the corresponding surfaces may be polished to a submicron level to ensure coupling therebetween. Optionally, the corresponding surfaces may be machined to a fine level where a nano-powder of hard material is introduced between the corresponding surfaces to ensure solid contact between them. Optionally the nano-powder may for example include but is not limited to 50 nm Zirconia particles, or the like. Optionally the two corresponding surfaces may be connected by brazing with thin silver compound.

Shockwave shaping portion 120 may interchangeably be referred to as a treatment head, treatment applicator or the like. Most preferably in order to provide for proper use a conducting fluid cushion (not shown) may be utilized to facilitate shockwave propagation from shaping portion 120 and onto the desired treatment surface.

Figure 1B:
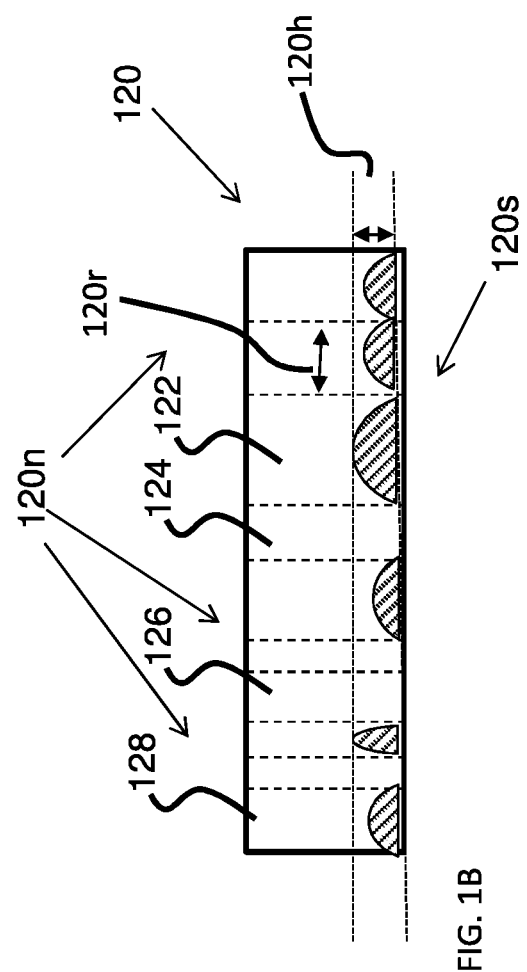

FIG. 1B provides a schematic block diagram of shaping device and/or adaptor 120. Shaping portion 120 is characterized in that it is provides for shaping the shockwaves generated by surface 110 prior to propagating the shockwave onto a treatment tissue site. Accordingly shaping portion 120 provides for configuring and shaping the shockwave delivered to the tissue site therein controlling the shockwave properties of system 100 and device 101 associated therewith.

Shaping portion 120 is preferably provides for controlling the shockwave penetration depth 20 the shape of shockwave wave front 10, therein. Shaping portion 120 is characterized in that it provides for treating large tissue treatment area having a diameter from about 30 mm up to about 300 mm. Optionally the treatment area may have a diameter of at least 80 mm and up to about 200 mm. Optionally shaping portion 120 is further characterized in that it provides for controlling the shockwave penetration depth that may be from about 50 mm up to about 200 mm.

Preferably shaping portion 120 is therefore adept at treating large tissue volume having a controlling area and penetration depth.

Shaping portion 120 is characterized in that its external surface 120s is non-linear and comprise at least one and more preferably a plurality of concave indentations 120n, 121-128 having variable radius and depth in order to control the shockwave propagating properties, emanating from external surface 120s.

Shaping portion 120 includes a plurality of round concave surface depressions 120n that are created as spherical sections, wherein the number of concave depressions 120n along the external surface 120s creates a corresponding number of shockwaves focal points and depths. Therein shaping device may be configured to produce highly variable and unique shockwave propagation wave fronts 10-18 to treat a large volume targeted tissue of the human or animal body.

Most preferably shaping portion 120 may be configured to have any number of concave depressions and/or recess 120n, wherein each concave recess may be configured according to its height 120h (or depth) and radius 120r, for example as shown.

Optionally shaping portion 120 may be provided from a single piece of metal and/or metal alloy that is associated with generating surface 110, as previously described, wherein the external surface 120s has been milled or otherwise shaped to include the required number of concave recess 120n.

Optionally shaping portion 120 may be provided from a plurality of individual segments 121-128 that may arranged and coupled, directly or indirectly, with generating surface 110 to build the required external surface 120s. Optionally individual concave segments 121-128 may be individually and/or directly coupled with generating surface 110. Optionally concave segments 121-128 may be indirectly coupled to generating surface 110 by utilizing a common connector (not shown) that is configured to be individually coupled with each concave segment 121-128 and commonly coupled to generating surface 110.

Shockwave shaping portion 120 may be provided in any geometric shape for example including but not limited to square, rectangular, polygonal of n sides wherein n is at least 2, ovoid, circular or the like geometric shape. Preferably shaping portion 120 is provided in the form of a spherical, circular and/or ovoid configuration having a diameter of up to about 100 mm. Optionally shaping portion may be provided with a diameter of about 50 mm. Optionally shaping portion may be provided with a diameter of up to about 150 mm. Optionally shaping portion may be provided with a diameter from about 5 mm and up to about 100 mm.

FIG. 2A-B show a side view, FIG. 2A, and a face on view, FIG. 2B, of an optional shaping portion 120 having a single concave segment depression 120n that is configured to produce a single shockwave focus.

FIG. 2C-D show a side view, FIG. 2C, and a face on view, FIG. 2D, of an optional shaping portion 120 having a plurality of concave segment depressions 120n that are individually configurable according to radius 120r and/or height 120h so as to create a unique shockwave front 10 pattern to treat a large tissue. The number of segment depressions 120n determine the number of possible shockwave foci. As shown in FIG. 2D, the plurality of concave segment depressions 120n may be arranged in any manner along external surface 120s. For example as shown, surface 120s comprises three groups of concave segments 120n that are arranged in a concentric manner, where each group may have individual parameters with respect to depression depth/height 120h and radius 120r.

When a flat projectile hits a flat shockwave generating surface, the energy is propagated mostly straight through the coupled shockwaves shaping portion. A large-diameter shockwaves shaping portion requires inventive design to distribute maximal SW energy to the parts that are remote from its middle, accordingly as shown in FIG. 3A-C the shockwave generating surface 110 is provided with a design so as to maximize shockwave generation in its ballistic impact with projectile 105.

FIG. 3A-C shows shaping portion 120 and generating surface 110 that are realized in the form of a of the high pressure ballistic shockwave instrument, where a projectile 105 is accelerated to collide with generating surface 110 to produce shockwaves 11-15 that propagate through surface 110 and onto shaping portion 120, as shown in FIG. 3A-B. FIG. 3A shows projectile 105 before hitting the shockwave generator surface 110, while FIG. 3B shows the instant of the impact and denotes the generated shockwaves 11-15 in non-limiting exemplary spatial directions, that propagate onto shaper 120.

Optionally and preferably generating surface 110 may be configured according to optional parameters for example including the materials and shape from which it is made in order to control the shockwaves produced therewith by way of the collision with projectile 105, to minimize the losses, to optimize the process of propagating the shockwaves from generator 110 to shaper 120.

Optionally generating surface 110 and shaper 120 may be configured relative to one another so as to control the propagation of the shockwaves and may therefore be provided from the same material, different materials a combination of materials. Optionally and preferably generating surface 110 and shaper 120 are provided from metal and/or a metal alloy.

FIG. 3C shows the importance of controlling the shape of generating surface 110 relative to the impact surface with projectile 105 so as to reduce losses, wherein the surface shown 110, having has fewer losses between generating surface 110 and shaper 120 as shockwaves 11 and 12 are not lost in the generating surface 110 of Optionally and preferably both the projectile 105 and shockwaves generating surface 110 are rounded to spherical sections that fit one another, for example as shown in FIG. 3A (before the impact) and FIG. 3B (at the moment of impact). In such a design, a larger projectile area hits a larger shockwaves generating surface area at the same time and the resultant shockwaves are distributed perpendicular to each point of the spherical section.

As known to those skilled in the art when a flat surface is required to hit another flat surface, it is virtually impossible to ensure that all points of the hitting surface will interact with corresponding points on the other flat surface. Using a convex spherical section for the projectile 105 and a concave spherical section for the SW generating surface 110 provides more interacting points between the surfaces, thus improving the impact efficiency of the shockwaves generator.

As is known to those skilled in the art, shockwaves propagate best in straight lines, so only shockwaves that are continuous solid medium between the shockwaves generating surface and the surface depressions of the shockwaves shaping portion will be focused and affect a SW treatment. As demonstrated in FIG. 3B, the thickness of the shockwaves generating surface and the geometry of the shockwaves shaping portion determine the efficiency of the shockwaves instrument. The shockwaves that are denoted by numbers 13, 14 and 15 are propagated toward surface depressions 120n, while the energy of those denoted by the numbers 11 and will be lost.

FIG. 3C shows that the amount of shockwaves that are not directed to surface depressions can be reduced by reducing the thickness of the shockwaves generating surface and adding width to the shockwaves generating portion to provide a solid medium between a larger part of the shockwaves generating surface and the surface depressions 120n. The sphere section angle of the projectile and shockwaves generator surfaces will determine the spatial angle of shockwaves propagation and ensure that most generated shockwaves can propagate through solid medium to shockwaves shaper surface 120.

Figure 4:
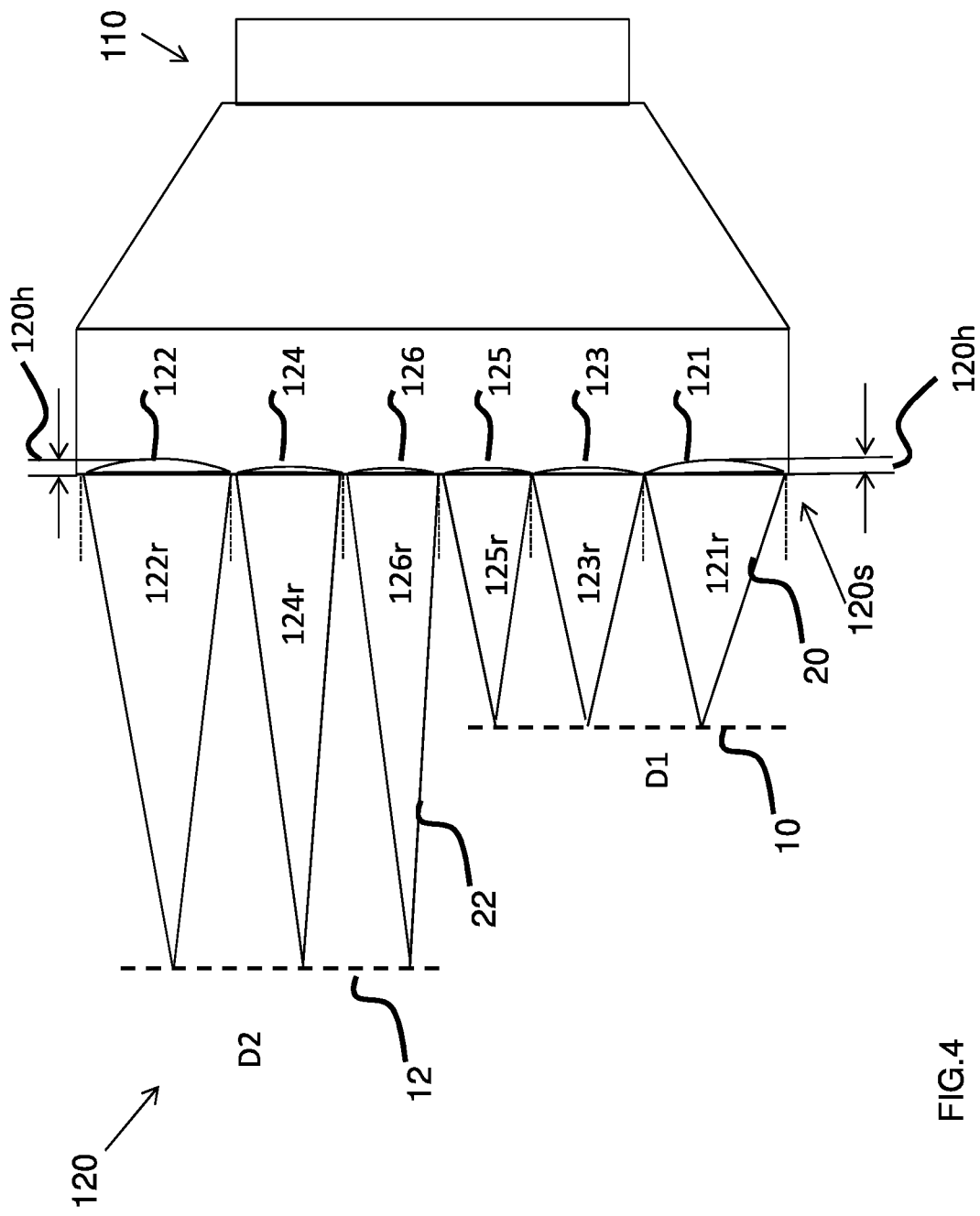
FIG. 4 is a schematic illustrative diagram of an exemplary shockwave shaping device according to embodiments of the present invention, the device configured to provide variable treatment depths.

FIG. 4 shows a shockwave shaping portion 120 of high pressure ballistic shockwave instrument 101 wherein external surface 120s is configured to have a plurality of individually configured depressions 120n, 121-126 that may be individually configured to have a radius 121r, 122r, 123r, 124r, 125r, 126r and height 120h to provide a shaping portion 120 that produces two distinct shockwave foci 10,12 at different depths D1,D2. Optionally any such configuration having at least one or more shockwave foci may be configured along external surface 120s.

Figure 5:
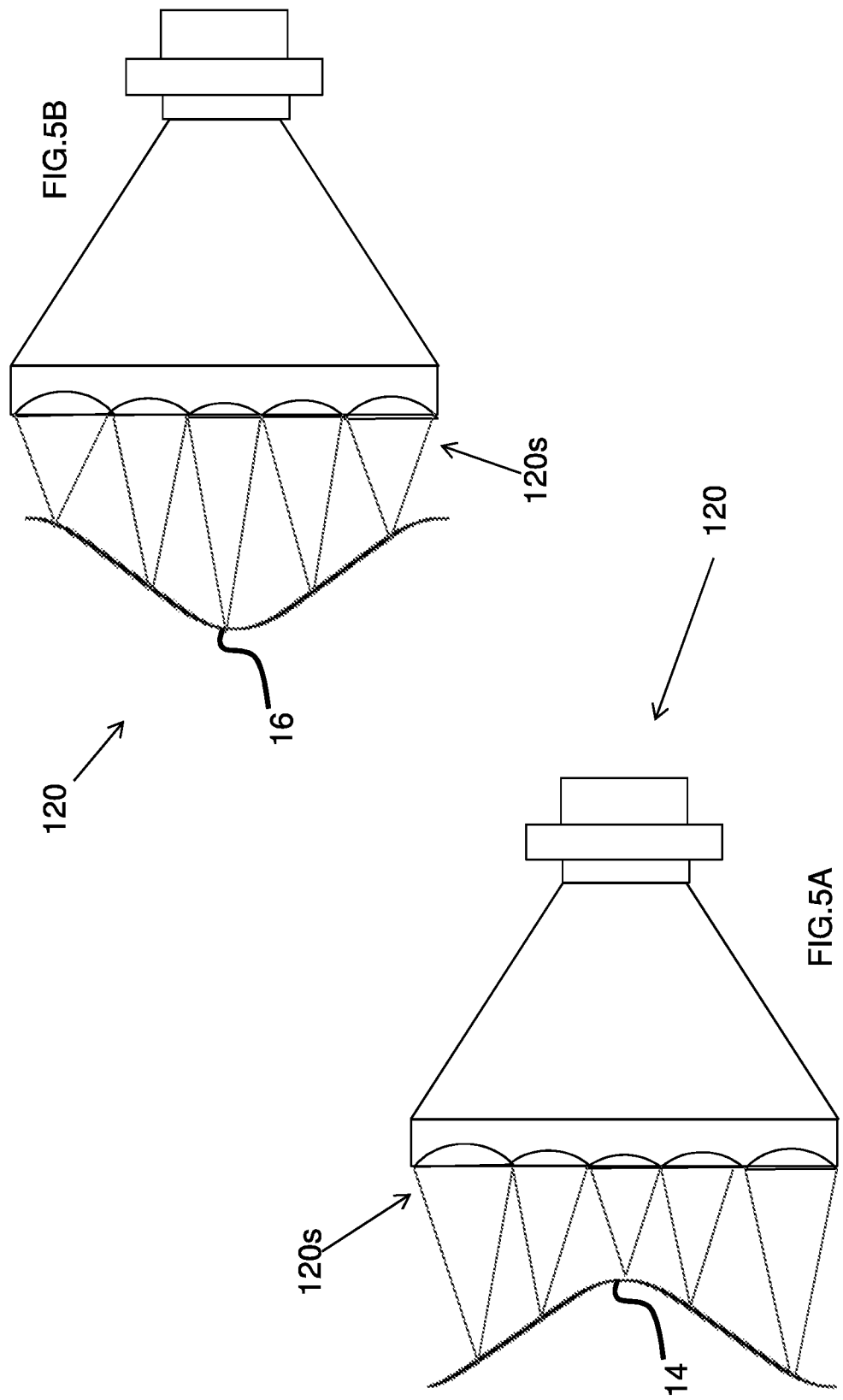
FIG. 5A-B are schematic illustrative diagrams of an exemplary shockwave shaping device for shockwave shaping according to embodiments of the present invention, the device configured to provide variable treatment depths.

FIG. 5A-B show a schematic illustration of a shockwave shaping portions 120, according to embodiments of the present invention wherein a plurality of concave depressions 120n may be utilized to renders two distinct sinusoidal three dimensional penetration patterns of shockwaves foci 16, 14. As previously described such three dimensional control is provided by controlling the parameters radius 120r and depth 120h of individual concave depressions 120n disposed about external surface 120s.

FIG. 5A shows such a concave focal surface 14 and FIG. 5B shows a convex focal surface 16. The SW treatment performed by such shockwaves shaping portion affects mainly the tissue volume that corresponds to the focal surface 14,16.

Figure 6:
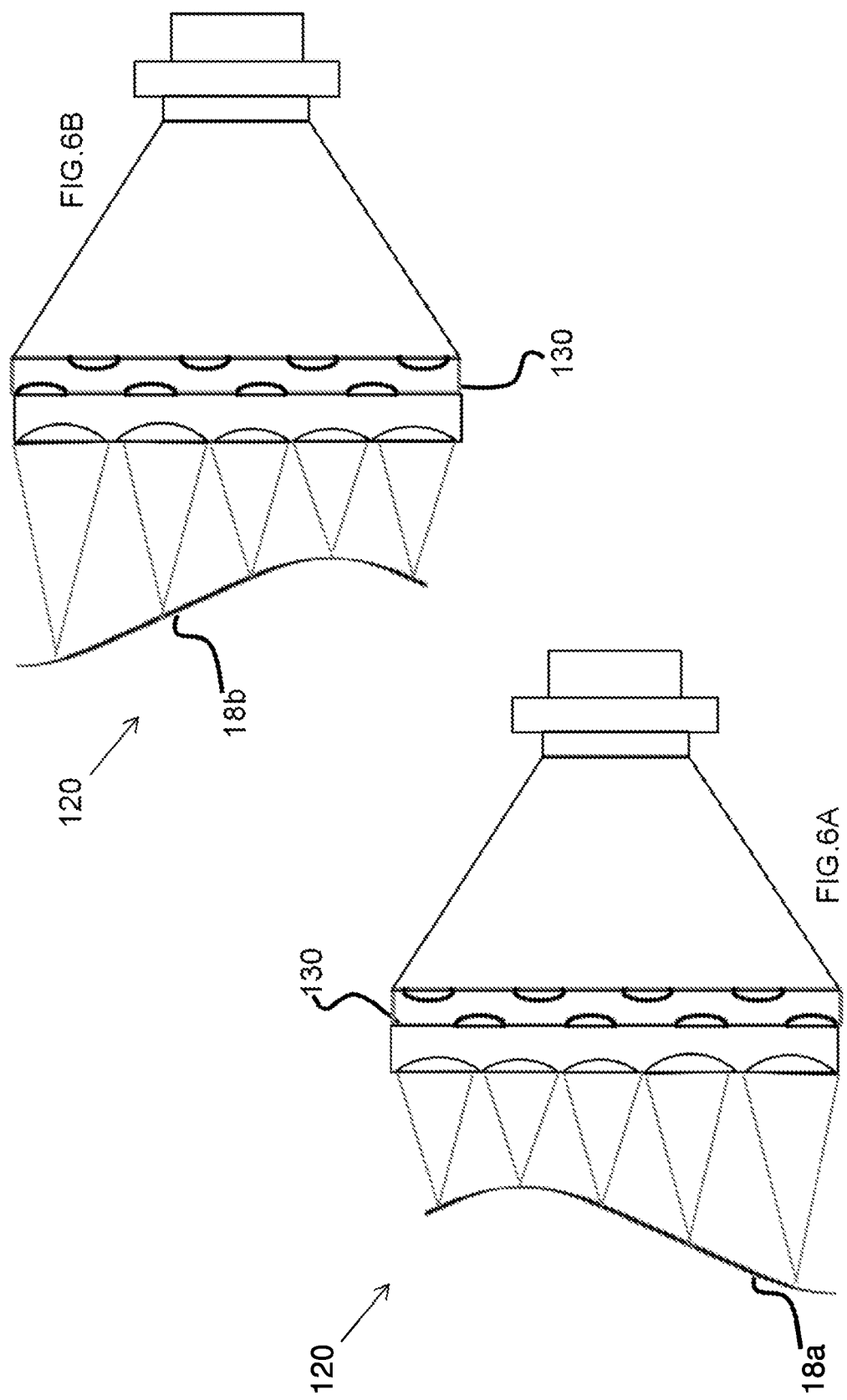
FIG. 6A-B are schematic illustrative diagrams of an exemplary shockwave shaping device for shockwave shaping according to embodiments of the present invention, device configured to provide variable treatment depths.

FIG. 6A-B shows an optional embodiment of the present invention wherein shaping portion 120 is configured to rotate by introducing a rotating stage 130 disposed between generating surface 110 and shaping portion 120, for example as shown. Rotating stage 130 is therefore configured to spin and/or rotate so as to provide for a moving shockwave foci pattern as shown 18a and 18b that have undergone 180 degree shift. By introducing rotating stage 130 allows for further shockwave delivery shaping providing a three dimensional penetration patterns of shockwaves foci. Such rotational shockwave pattern facilitate the production of a massage like and kneading effect at the tissue treatment site.

Optionally the revolution of stage 130 is synchronized with shockwave generation 110 so that each pulse occurs when the revolving part is stationary.

As known to those skilled in the art—shockwaves are propagated best through a continuous, solid medium. A standard rotation mechanism that is designed on the basis of ball bearings or rollers will transfer only a small part of shockwaves energy. Accordingly rotating stage 130 is optionally and preferably based on the use of slider bearings that ensure a fully continuous contact between the fixed portion, generating surface 110, and rotating portion, shaping apparatus 120, therein maximizing the transfer and propagation of shockwaves between the parts.

Optionally rotating motion of stage 130 is an indexing motion, where the rotation is affected for a specific angle then stopped and locked for the duration of a shockwave pulse and then rotation starts again. To ensure best shockwave propagation through the interface between the rotated portion 120 and fixed portion 110, both touching surfaces are finely machined for best coupling contact between them. For minimizing the friction between the coupled surfaces during motion and maintain the optimized coupling of the rotated and fixed parts, the sliding rotation may be done over a very thin air cushion between the two parts. This cushion is inflated for the duration of motion and deflated for the duration of generating a shockwave pulse.

Optionally the air cushion may be implemented by incorporating an assembly of air nozzles that transfer air at high enough pressure to disengage the fixed part from rotating part and essentially eliminate the motion friction between those parts. Optionally the air may be pushed in and out the air nozzles by a fast moving piston that serves as a virtually closed system and creates an air cushion having a thickness that is in the order of 25 micrometer that is produced within about 10 milliseconds—thus enabling 90% utilization in a 20 focal points, 5 Hz protocol.

Figure 7:
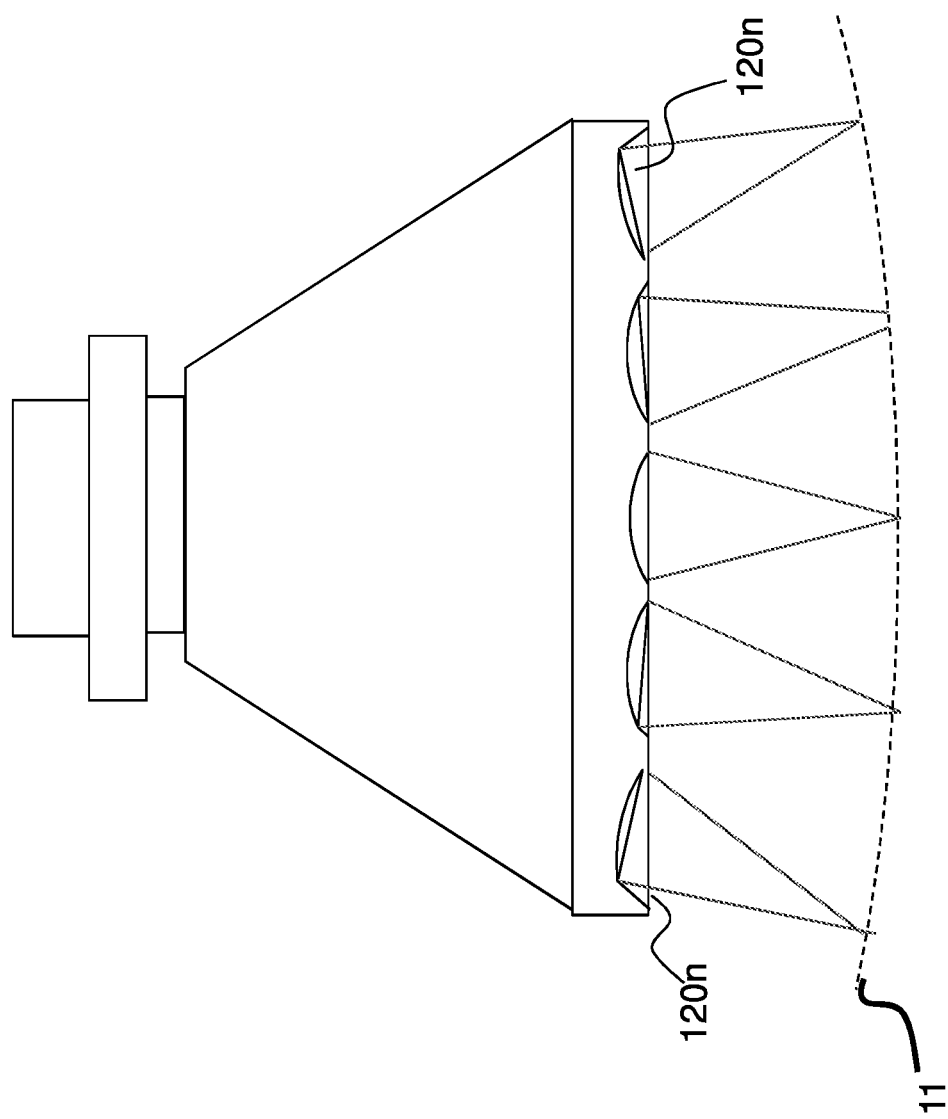
FIG. 7 is a schematic illustrative diagram of an exemplary shockwave shaping device for shockwave shaping according to embodiments of the present invention, device configured to provide variable treatment depths.

FIG. 7 shows an optional embodiment where at least one or more concave recess 120n is provided at an angle therein providing a curved shockwave front 11 for example as shown. Such angulation of concave recess 120n further provide for angled focused shockwave that produces high-pressure shockwaves pulses that can be focused in diagonal directions outside the perimeter of the shockwaves shaping portion.

Figure 8:
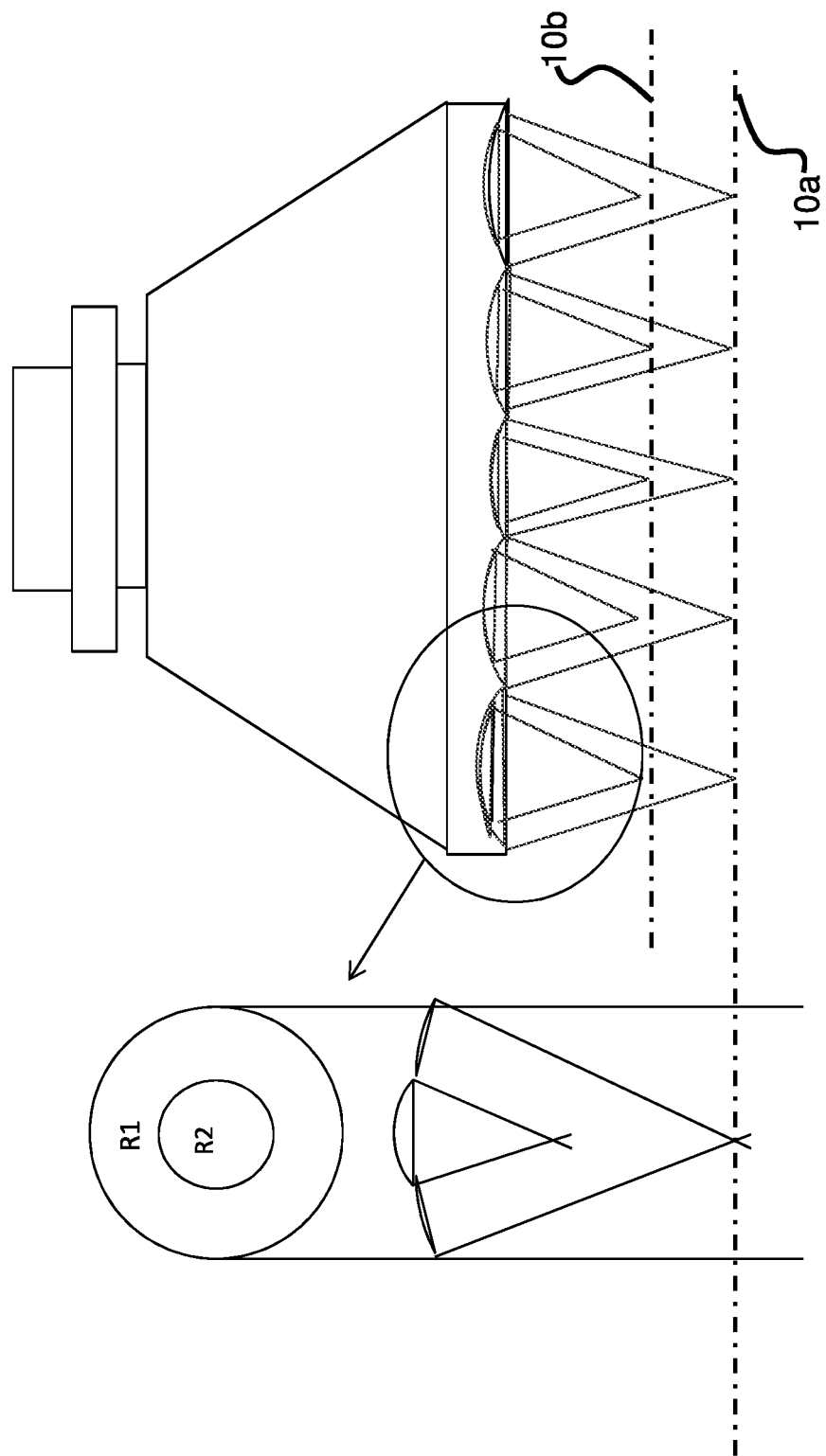
FIG. 8 is a schematic illustrative diagram of an exemplary shockwave shaping device for shockwave shaping according to embodiments of the present invention, device configured to provide variable treatment depths.

FIG. 8 shows a further optional concave depression 120n that provided a dual depth shockwave penetration pattern 10a, 10b. Such dual depth shockwave penetration pattern is provided by utilizing a concave recess that has two distinct radii R1 and R2.

The surface depressions 102n in the shockwave shaping portion 120 may be dual sphere that are concentric but have different radii, therein producing a sphere within a sphere with different sphere radius for each, for example as shown. The benefit of such interlaced spheres with different radii is in the ability of shockwaves treatment an entire vertical focal volume of an extended depth, such as in a non-limiting example—treatment of substantially the full volume of a bovine udder.

Figure 9:
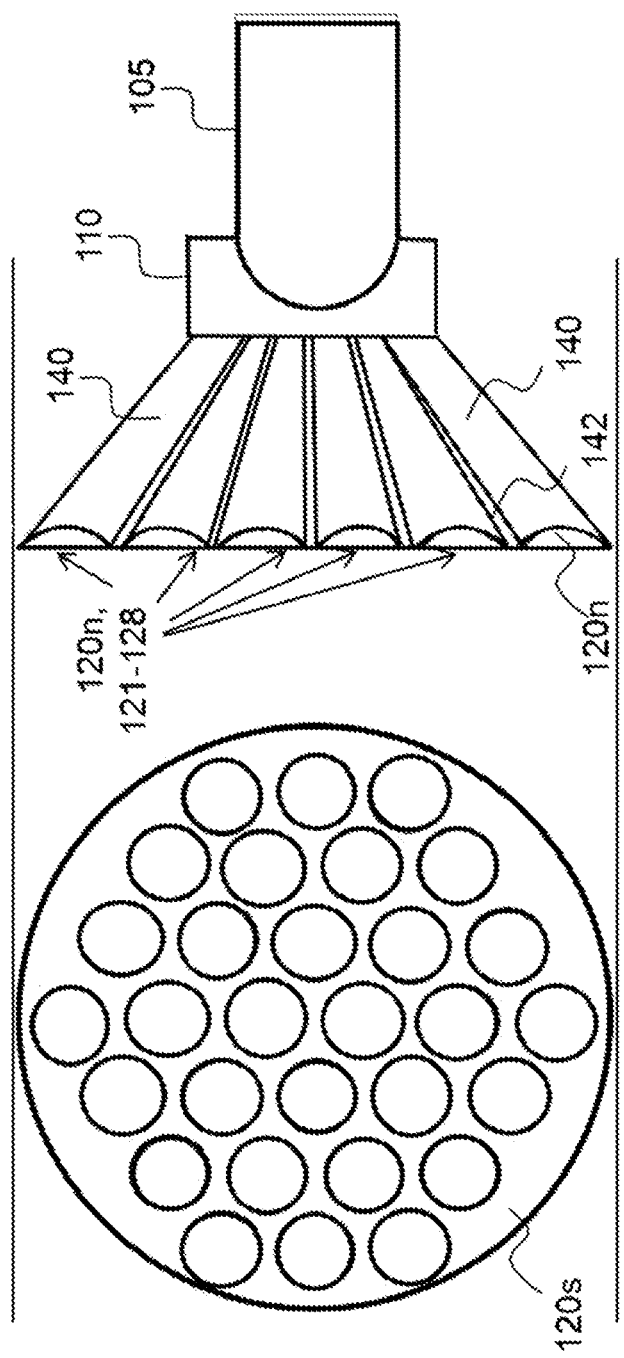
FIG. 9 is a schematic illustrative diagram of an exemplary shockwave shaping device according to optional embodiments of the present invention.

FIG. 9 shows an optional shockwave shaping apparatus 120 that is composed of a plurality of individual concave depressions 120n forming the external surface 120s, however each concave depression 121-128 has a conical sections body 140 extending from shockwave generating surface 110, wherein each conical body section 140 is separate from an adjacent member with an air pocket 142. Optionally, shaping apparatus 120 as shown may be machined from a solid volume for example by way of Electric Discharge Machine (EDM) that erodes by wire disconnecting individual conical section 140 volumes in the solid shockwaves shaper 120 therein leaving space between the surface depressions, thus creating air gaps 142 that shield each section 140 from shockwaves generated and/or propagating in an adjacent sections 140. In such a non-limiting example, the eroded sections 142 do not extend to the external surface 120s of the shockwaves shaping portion 120 that is coupled to the shockwaves generator 110, but their depth is enough for the disparity in timing of shockwave pulses and for reduction of the interference effect.

FIG. 10 is a schematic diagram of a shockwaves system 100 that is functionally associated with an automated milking system 200 and/or milking robot. Such a system is adept to treat a large tissue volume, for example in the form of a cow udder. Providing shockwave treatment to the cow udder 206 with the device an system according to embodiments of the present invention may provide for treating a herd of cows in contributing to the overall herd population health and for preventing and/or treating cows exhibiting mastitis.

System 200 comprising a milking machine and/or robot having a plurality of suction cups 202 that are configured to associate with a teat 204 of an udder 206, as is known in the art. Optionally suction cups 202 may be fits on a stage 210 onto which shockwave system 100 according to embodiments of the present invention is fit. Preferably stage 210 provides for simultaneously and/or collectively applying and/or associating suction cups 202 and shockwave system 100 onto udder 206. Such that when suction cups 202 are deployed onto teat 204 allows shockwave system 100 to associate over udder 206, for example as shown.

Optionally stage 210 may be further fit with a mounting member and/or support member 212 that facilitates secure and proper coupling between shockwave system 100 and udder 206. Optionally mounting member 212 may be provided in the form of an air piston and/or spring. Optionally a mounting member 212 in the form of an air piston may provide for pressing the shockwave system 100 against the bovine udder 206, wherein the air piston is activated after the attachment of suction cups 202 onto the bovine teats 204 and after the manual positioning adjustment of shockwave system 100. Preferably, a mounting member 212 in the form of an air piston provides controlled and constant pressure for optimal propagation of shockwaves onto the target udder 206.

Optionally system 100 may comprise imagery system 50, as previously described, to facilitate placement onto udder 206. Optionally imagery system 50 may be provided in the form of a laser pointer to provide a visual indication of the center of the treatment target to facilitate placement of the shockwave system.

Example: Mastitis

A cow's udder is composed of two halves, each of which has two teats and each teat drains a separate gland referred to as a quarter. The quarters are separated by connective tissue and each has separate milk collecting system. Each quarter may be infected by mastitis that may go unrecognized until after milking has been undertaken. Milk from a cow exhibiting mastitis cannot be used and usually by the time it is discovered the milk is lost, leading to financial losses. Mastitis could further lead to loss of the herd member representing a greater financial loss to the farmer.

The system of the present invention may be utilized to prevent and/or treat mastitis as the shaping portion 120 provides for treatment of a large and deep tissue area such as a cow udder.

Almost any bacterial or mycotic organism that can cause infection can cause mastitis. However, most infections are caused by various species of streptococci, staphylococci, and gram-negative rods, especially lactose-fermenting organisms of enteric origin, commonly termed coliforms.

Intra-mammary infections are often described as subclinical or clinical mastitis. Subclinical mastitis is the presence of an infection without apparent signs of local inflammation or systemic involvement.

Chronic infections persist for at least 2 months. Once established, many of these infections persist for entire lactations or the life of the cow.

Detection of both clinical and subclinical mastitis is commonly done by examination of milk for somatic cell counts, which are positively correlated with the presence of infection. Cows with a somatic cell count of ≥280,000 cells/mL (≥ a linear score of 5) have generally a >80% chance of being infected.

Clinical mastitis: typically displays disorder only in one udder quarter at a time, although Mycoplasma may affect multiple quarters.

Cure rate with antibiotic therapy during lactation is very low; infected cows that become chronic cases often have to be culled. Accordingly, the system according to embodiments of the present invention provide a solution for treating mastitis.

Subclinical Mastitis: All dairy herds have cows with subclinical mastitis; however, the prevalence of infected cows varies from 15-75%, and quarters from 5-40%.

The magnitude of subclinical mastitis towards the economic loss is conspicuous from the fact that in USA, it is estimated that such losses are responsible for 60 to 70% of total economic losses associated with all mastitis infections.

*S. aureus* infection remains the largest mastitis problem of dairy animals. The infection usually continues as subclinical hence, control measures take many years to reduce the proportion of infected quarters.

Chronic Mastitis: Chronic mastitis is an inflammatory process that exists for months and may persist from one lactation cycle to another. It is manifested for the most part as sub-clinical and may flare-up periodically as sub-acute or acute form for a short period of time. Adult lactating cattle are most at risk for infection, either while lactating or during the dry period.

Many subclinical cases selected as potential therapy candidates have chronic infections; particularly in the case of *S aureus*, prediction of therapeutic outcome by in vitro testing is unreliable. Drug distribution following intramammary administration may not be adequate due to extensive fibrosis and micro-abscess formation in the gland; it is critical to assess the cow's immune status from a perspective of duration of infection, number of quarters infected, and other variables.

Cellular Response: Bacteria in the teat are recognized by macrophages and lymphocytes that trigger an alarm that induces a host response that leads to huge numbers of bacteria-killing cells called PMNs (polymorphonuclear leucocytes, mainly neutrophils) entering the milk. In normal milk they are present in such low numbers as to be ineffective against a heavy bacterial load. The inflow of PMNs from the capillaries in the teat wall and udder into the cisterns and ducts is caused by chemotaxin signaling.

Typical treatment is with antibacterial drugs for All 4 quarters of infected cows to ensure elimination of the pathogen and to prevent possible cross-infection of a non-infected quarter. Cure rates can often be 75-90%. Treated cows must be monitored by somatic cell counts and bacteriology. Usually, 30-day monitoring intervals are successful.

Many streptococcal infections are not as easily cured as those caused by *S agalactiae*. Generally, subclinical infections caused by *S uberis* and *S dysgalactiae* should be preferentially treated at the end of lactation with intramammary infusions of commercial dry cow products. Cure rates at this time may exceed 75%. Cure rate with antibiotic therapy during lactation is very low and infected cows that become chronic cases and are to be culled.

The presence of Milk leukocytes (PMN) in gland cell milk is to protect the mammary gland from infections and to provide signaling function in the infected gland (Paape et al., 2000). Macrophages and PMN are phagocytic cells and they swallow and kill bacteria. Lymphocytes that consist of both B-cells and T-cells, play important role in immune reactions in response to initial infection. When bacteria enter the mammary gland through the teat canal and multiply in milk, an inflammatory response (mastitis) takes place. Bacteria affect the function of the mammary epithelium and also interact with the cells in milk, particularly macrophages and stimulate the production of many mediators inflammation (Zecconi et al., 1997). Some of the mediators are complement components, prostaglandins, leukotrienes, histamine, serotonin, interleukins, tumor necrosis factor, interferon and other cytokines (Anderson and Heneghan, 1979.( Cost of Mastitis Mastitis is the most costly disease of dairy cows and the economic loss is due to discarded milk, early culling, drug costs, veterinary costs, increased labor and primarily decreased quantity and quality of milk and manufactured milk products (DeGraves and Fetrow, 1991). The loss of milk production due to mastitis is estimated in many different ways and one of the most important methods is based on milk SCC (Seegers et al., 2003.( About 70% of the production losses due to subclinical mastitis are attributed to decreased milk production (Moniri et al., 2007). Subclinical mastitis has higher economic burden than clinical mastitis for the reason that losses associated with subclinical infection are widespread and less treated. In quarters affected with subclinical mastitis, total milk loss is on an average 10-26.%

Mastitis cannot be eradicated from a herd and no complete recovery is forecast for a quarter affected with clinical mastitis. The economic loss due to decreased milk production, increased milk replacement cost, discarded milk, drug costs, veterinary fees and labor cost aggregates to about 10% of total value of milk sales.

The estimates of the cost of clinical mastitis is $107 US per clinical prevalence—of which, 70% of the cost is connected with decreased milk production and milk withheld from the market, over 20% with drugs, veterinary costs and replacement cost and with labor (Ahl et al., 1989; Halasa et al., 2007.( Having described a specific preferred embodiment of the invention with reference to the accompanying drawings, it will be appreciated that the present invention is not limited to that precise embodiment and that various changes and modifications can be effected therein by one of ordinary skill in the art without departing from the scope or spirit of the invention defined by the appended claims.

Further modifications of the invention will also occur to persons skilled in the art and all such are deemed to fall within the spirit and scope of the invention as defined by the appended claims.

While the invention has been described with respect to a limited number of embodiment, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not described to limit the invention to the exact construction and operation shown and described and accordingly, all suitable modifications and equivalents may be resorted to, falling within the scope of the invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Citation or identification of any reference in this application shall not be construed as an admission that such reference is available as prior art to the invention.

Section headings are used herein to ease understanding of the specification and should not be construed as necessarily limiting.

While the invention has been described with respect to a limited number of embodiments, it will be appreciated that many variations, modifications and other applications of the invention may be made.

What is claimed is:

1. A ballistic shockwave system including a ballistic shockwave device configured to generate a ballistic collision between a projectile and a shockwave generating portion using a high pressure gaseous source having operating pressure of up to about 200 bar; the shockwave generating portion is coupled to a shockwave shaping portion that is provided to direct the generated shockwaves to a targeted tissue treatment site, said shaping portion comprises an external shaping surface formed from a plurality of concave focal surface depressions, wherein each of said concave focal surface depressions are individually configurable according to a diameter and depth, and wherein said configurable diameter and depth provide for determining a focal length and a penetration depth of a propagated shockwave, wherein the propagated shockwave treats a tissue volume in three dimensions and wherein the shaping portion is provided with an overall diameter of up to 100 mm; and a rotating stage associated between said shockwave shaping portion and said shockwave generating portion wherein said rotating stage provides from rotating said shockwave shaping portion.

2. The system of claim 1 further comprising a sensor module comprising a locating sensor.

3. The system of claim 2 further comprising a treatment locating sensor including a laser pointer that provides visual indication of a center of the treatment target to facilitate placement of the ballistic shockwave system.

4. The system of claim 1 further comprising a feedback sensor.

5. The system of claim 4 wherein said feedback sensor is a fast pressure sensor that measures time-calibrated signal on a surface of the shockwaves shaping portion that indicates shockwaves reflection from the target tissue treatment site.

6. The system of claim 5 wherein the pressure sensor signal is read during a predetermined window of time that is centered on an expected duration between a forward-going shockwave signal and a backward reflection from a different tissue.

7. The system of claim 1 wherein said shockwaves shaping portion is configured to produce a therapeutic shockwave for a targeted tissue treatment site having dimensions selected from: 50 mm to 300 mm in depth, 50 mm to 200 mm in depth, 120 mm to 250 mm in diameter and 50 mm to 150 mm in depth.

8. The system of claim 1 wherein corresponding surfaces of said shaping portion and generating portion correspond with one another such that they are seamless with one another.

9. The system of claim 1 wherein said concave focal surface depressions are spherical sections.

10. The system of claim 9 wherein a radius of said concave focal surface depressions determines the shockwave penetration depth.

11. The system of claim 9 wherein said shockwave shaping portion features a plurality of round surface depressions of different radii.

12. The system of claim 1 wherein said shockwave shaping portion features a plurality of concave surface depressions including at least two groups of concave depressions each group having a different radii.

13. The system of claim 1 wherein said shockwave shaping portion is configured to provide for targeted treatment of an area having a diameter selected from between 30 mm and 300 mm, larger than 80 mm, from 80 mm up to 200 mm, or lower than 200 mm.

14. The system of claim 1 wherein each of said plurality of concave surface depressions are configured to form a pattern.

15. The system of claim 1 wherein each of said plurality concave surface depressions are configured according to the treatment area.

16. The system of claim 1 wherein each of said plurality of concave surface depressions are configured to shape the shockwaves for treatment of a cow udder.

17. The system of claim 1 wherein said tissue volume is a quarter of a bovine udder.

18. The system of claim 1 wherein ballistic shockwave device is configured to be associated with at least one of an automated milking device or a milking robot along and least one or more teat milking suction cups.

19. The system of claim 1 wherein the ballistic shockwave device is disposed along a support member, the support member further associated with at least one or more teat milking suction cups that are coupled to an automated milking device or a milking robot.

20. The system of claim 19, wherein said mounting support member further comprises a spring to ensure that the shockwave generating portion is pressed against a bovine udder.

21. The system of claim 19 wherein a location of the shockwave shaping portion is adjustable along the suction cup so as to define an exact position and orientation of the shockwaves system relative to an udder.

22. The system of claim 1 wherein said ballistic shockwave system is integrated into a bovine milking processing line.

23. The system of claim 1 wherein said targeted tissue volume is selected from: a human trochanter fascia, a piriformis muscle, or a human groin muscle.

24. The system of claim 1 wherein said concave focal surface depressions is configured to form a concentric multi-sphere depression having at least two interlaced spheres radii, wherein each radii produces an individual focal length that are superimposed to produce a multi-focal zone concave focal surface depression.

25. A method for extracorporeal high pressure shockwave treatment of biological tissue having a diameter from about 30 mm up to about 300 mm with the system of claim 1.

26. The method of claim 25 wherein said biological tissue is selected from: human musculoskeletal treatment targets, a human trochanter fascia, a piriformis muscle, or a human groin muscle.

27. The method of claim 25 wherein said biological tissue is an animal tissue selected from the group: horse, bovine, at least a portion of a bovine udder, a quarter of a bovine udder, a buffalo udder quarter, goat udder halves, sheep udder halves, or tendons and ligaments to reduce stress and limping.

28. The method of claim 25 utilized for treatment of at least a portion of a bovine udder that is infected with at least one selected from: chronic mastitis, sub-clinical mastitis, a bovine udder quarter that yields reduced quantity of milk, a bovine udder that yields reduced protein levels in the milk, or treatment of bovine udder that yields reduced sugar levels in the milk.

29. A ballistic shockwave system including a ballistic shockwave device that is disposed along a support member featuring a spring, the support member further associated with at least one or more teat milking suction cups that are coupled to an automated milking device or a milking robot; wherein said spring ensures that a shockwave generating portion of the ballistic shockwave device is pressed against a bovine udder;

said ballistic shockwave device is configured to generate a ballistic collision between a projectile and the shockwave generating portion using a high pressure gaseous source having operating pressure of up to about 200 bar; the shockwave generating portion is coupled to a shockwave shaping portion that is provided to direct the generated shockwaves to a targeted tissue treatment site, said shaping portion comprises an external shaping surface formed from a plurality of concave focal surface depressions, wherein each of said concave focal surface depressions are individually configurable according to a diameter and depth, and wherein said configurable diameter and depth provide for determining a focal length and a penetration depth of a propagated shockwave, wherein the shockwave treats a tissue volume in three dimensions and wherein the shaping portion is provided with an overall diameter of up to 100 mm.

30. The system of claim 29 wherein a location of the shockwave shaping portion is adjustable along the suction cup so as to define an exact position and orientation of the shockwaves system relative to an udder.

31. The system of claim 29 further comprising a treatment locating sensor including a laser pointer that provides visual indication of a center of the treatment target to facilitate placement of the ballistic shockwave system.

32. The system of claim 29 wherein said shockwave shaping portion features a plurality of concave surface depressions including at least two groups of concave depressions each group having a different radii.

* * * * *